United States Patent [19]

Hirashima

[11] Patent Number: 6,060,258
[45] Date of Patent: May 9, 2000

[54] NEUTROPHIL CHEMOTACTIC LYMPHOKINE, AND METHOD FOR THE DIAGNOSIS OF DRUG HYPERSENSITIVE GRANULOCYTOPENIA USING THE SAME

[75] Inventor: Mitsuomi Hirashima, Takamatsu, Japan

[73] Assignee: Otsuka Pharmaceutical Co., Ltd., Tokyo, Japan

[21] Appl. No.: 09/043,670

[22] PCT Filed: Sep. 26, 1996

[86] PCT No.: PCT/JP96/02779

§ 371 Date: Mar. 25, 1998

§ 102(e) Date: Mar. 25, 1998

[87] PCT Pub. No.: WO97/12054

PCT Pub. Date: Apr. 3, 1997

[30] Foreign Application Priority Data

Sep. 28, 1995 [JP] Japan .................................... 7-250753
Dec. 28, 1995 [JP] Japan .................................... 7-343201

[51] Int. Cl.[7] ........................... C07K 14/52; G01N 33/53
[52] U.S. Cl. ........................ 435/7.24; 435/7.2; 435/7.21; 435/325; 435/372; 435/372.3; 435/375; 530/351
[58] Field of Search .............................. 530/351; 435/7.2, 435/7.21, 7.24, 325, 372, 372.3, 375

[56] References Cited

U.S. PATENT DOCUMENTS 5,679,356 10/1997 Bonnem et al. ..................... 424/278.1

OTHER PUBLICATIONS

Japanese Journal of Allergology, "Allergy", vol. 44, No. 8, Aug. 1995 (with English translation).

The Abstract #665, Volume for the Ninth International Congress of Immunology, Jul. 1995, San Francisco, CA Nishi Yama et al.

International Search Report.

*Primary Examiner*—Prema Mertz
*Attorney, Agent, or Firm*—Sughrue, Mion, Zinn, Macpeak & Seas, PLLC

[57] ABSTRACT

The invention provides a neutrophil chemotactic lymphokine having an isoelectric point at 6.8-7.0, a cell line producing the lymphokine, and an agent for diagnosing drug-induced granulocytopenia, which comprises the lymphokine. When the diagnostic agent according to the invention is used for a patient, whether the patient has a possibility that drug-induced granulocytopenia may be caused or not can be diagnosed prior to the administration of a drug. Therefore, the patient can be safely treated without causing any side effect.

3 Claims, 3 Drawing Sheets

NEUTROPHIL CHEMOTACTIC LYMPHOKINE, AND METHOD FOR THE DIAGNOSIS OF DRUG HYPERSENSITIVE GRANULOCYTOPENIA USING THE SAME

TECHNICAL FIELD

The present invention relates to a novel neutrophil chemotactic lymphokine and a diagnostic agent for diagnosing an attack of drug-induced granulocytopenia comprising this lymphokine.

BACKGROUND ART

Granulocytopenia refers to a condition that the number of granulocytes in peripheral blood is decreased, and is a concept including agranulocytosis marked by severe decrease or loss in granulocytes and accompanied by a grave condition. Of these, the agranulocytosis has a high mortality due to infectious diseases.

As causes of the granulocytopenia, have been known the attack attending on other various diseases, administration of a drug, and the like. Of these, the granulocytopenia caused by the drug includes drug-induced granulocytopenia. The attack of the drug-induced granulocytopenia cannot be predicted prior to the administration of the drug under the circumstances. Further, no drug for treating the drug-induced granulocytopenia after the attack has been known, and so its treatment only depends on stopping the administration of a causative drug under the circumstances.

Accordingly, it is an object of the present invention to provide a diagnostic agent capable of predicting an attack of drug-induced granulocytopenia.

DISCLOSURE OF THE INVENTION

In view of the foregoing circumstances, the present inventors have paid attention to granulocyte chemotactic factors, particularly, neutrophil chemotactic lymphokines and carried out a varied investigation as to their diversity and specificity. As a result, it has been found that a plurality of subspecies different in isoelectric point from one other exist in the neutrophil chemotactic lymphokines. The inventors have succeeded in isolating a novel lymphokine not reported heretofore therefrom. It has also been found that there is a correlation between the chemotaxis of a neutrophil by such a novel lymphokine and the attack of drug-induced granulocytopenia, namely, an individual having a neutrophil low in chemotactic capability to the lymphokine is attacked by drug-induced granulocytopenia, and that the same correlation as described above is also present in a GM-CSF (granulocyte-macrophage colony-stimulating factor), thus leading to completion of the present invention.

According to the present invention, there are thus provided a neutrophil chemotactic lymphokine having an isoelectric point at 6.8–7.0 and a cell line which produces such a lymphokine.

According to the present invention, there are also provided an agent and a kit for diagnosing drug-induced granulocytopenia, which comprises the lymphokine described above.

According to the present invention, there are further provided an agent and a kit for diagnosing drug-induced granulocytopenia, which comprises a GM-CSF.

BEST MODE FOR CARRYING OUT THE INVENTION

Figure 1:
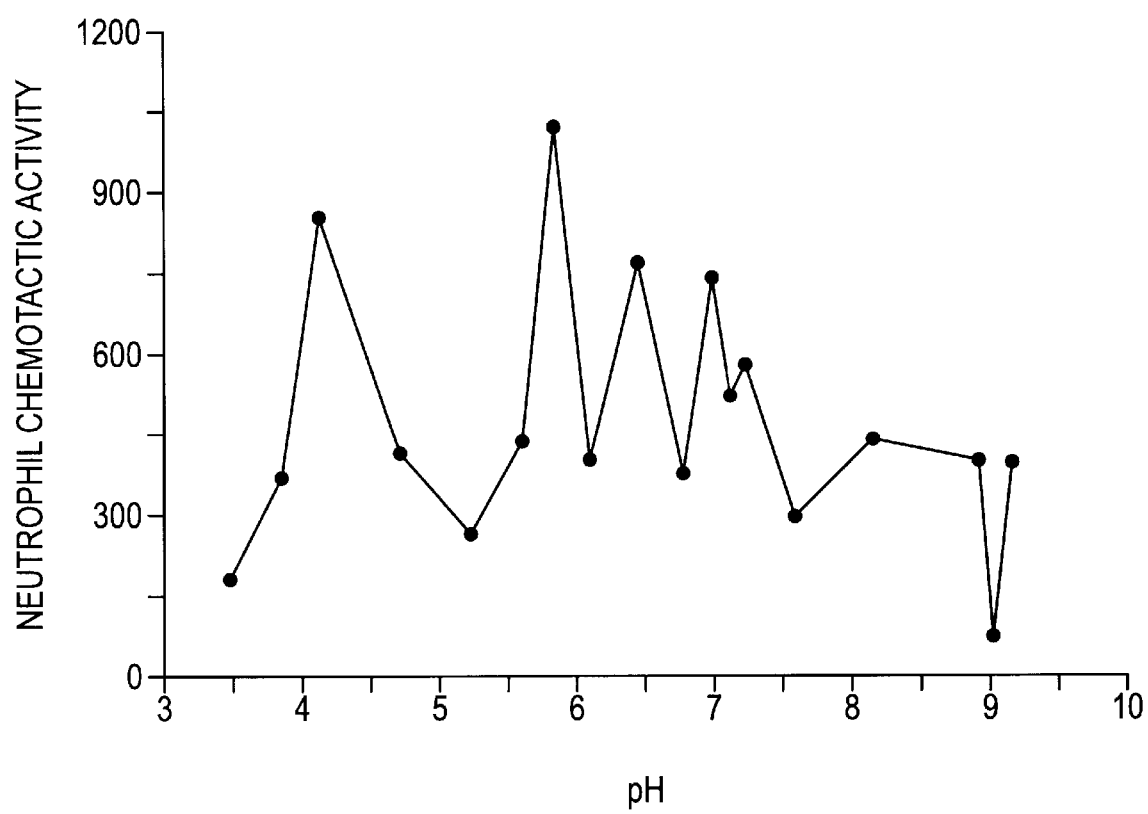
FIG. 1 diagrammatically illustrates a relationship between isoelectric focusing fractions of CFR-24 culture solution and neutrophil chemotactic activity, FIG. 2 diagrammatically illustrates relationships between chemotaxis indices (CI) of a neutrophil to NCL-4 and GM-CSF and specimens, and FIG. 3 diagrammatically illustrates relationships between expression rates of CD11b in a neutrophil by NCL-4 and GM-CSF and specimens.

The neutrophil chemotactic lymphokine (hereinafter referred to as NCL-4) having an isoelectric point at 6.8–7.0 according to the present invention can be obtained from a T cell line obtained by transforming, for example, a normal T cell with a virus.

Here, the NCL-4 producing T cell line can be obtained by coculturing, for example, a normal human mononuclear leukocyte together with a human adult T cell leukemia cell line (for example, MT2) and establishing a T cell line transformed with a virus produced by the leukemia cell line.

In order to collect NCL-4 from this virus-transformed T cell line, it is only necessary to culture this cell line, conduct isoelectric focusing of the culture solution thereof using neutrophil chemotactic capability as an index and collect a fraction having an isoelectric point of 6.8–7.0.

The NCL-4 thus obtained has the following properties:

(1) having neutrophil chemotactic capability;
(2) having an isoelectric point (pI) of 6.8–7.0;
(3) increasing neither intracellular calcium ion concentration nor cell membrane potential;
(4) inhibiting apoptosis (decrease in CD16);
(5) having the ability to express CD11b;
(6) having no affinity for heparin; and
(7) having a molecular weight of 50 kd to 80 kd (as measured by gel filtration).

The GM-CSF useful in the practice of the present invention is a sort of lymphokine and has been known as a hematopoietic regulatory factor in vivo, but has not been known to be used as a diagnostic agent for drug-induced granulocytopenia.

The GM-CSF itself used in the present invention is known, can be prepared in accordance with a method known per se in the art (for example, The Journal of Immunology, Vol. 137, P. 3584 (1986), etc.) and is also commercially available.

In order to diagnose drug-induced granulocytopenia using the diagnostic agent according to the present invention, which comprises the NCL-4 or GM-CSF, the reactivity of a neutrophil of a patient, to which a drug will be administered, may be determined in the presence of the diagnostic agent according to the present invention. As a result, it may be diagnosed that the patient has a high possibility of being attacked by drug-induced granulocytopenia if the reactivity of the neutrophil of the patient is low.

The reactivity of the neutrophil can be determined or confirmed in accordance with a method known per se in the art. For example, it can be performed by a method making use of the chemotaxis or of the expression rate of CD11b (The Journal of Cell Biology, Vol. 120, No. 2, p. 545 (1993)) of the neutrophil as an index.

According to the testing method of neutrophil chemotaxis, the reactivity can be determined in accordance with the conventional means except that the diagnostic agent according to the present invention is used as a chemotactic factor. Examples of such a testing method of neutrophil chemotaxis include a micropore filter method and an agarose method (Respiration, Vol. 4, No. 10, p. 1221 (1985); Journal of Leukocyte Biology, Vol. 51, p.617 (1992), etc.).

The result of the test of neutrophil chemotaxis is preferably evaluated, for example, by using chemotaxis index (CI value; chemotactic capability to the diagnostic agent according to present invention/chemotactic capability to a control) as an index.

Further, the measurement of the expression rate of CD11b may also be conducted in a method known per se in the art, and can be easily performed by usual immunological analysis or assay making use of a specific antibody thereof. Incidentally, the anti-CD11b antibody can be prepared in accordance with a method known per se in the art or is also commercially available.

The object of the diagnostic agent according to the present invention is preferably a patient to which a drug already reported to cause drug-induced granulocytopenia or a drug having the possibility thereof will be administered.

No particular limitation is imposed on the preparation form of the diagnostic agent according to the present invention so far as the agent comprises the above-described NCL-4 or GM-CSF. For example, the agent may be provided as a solution with the NCL-4 or GM-CSF dissolved in a buffer solution. The diagnostic agent according to the present invention may also be used as a kit for a clinical test in combination with other reagents, buffers, necessary instruments and the like. Upon diagnosis, the diagnostic agent comprising NCL-4 and the diagnostic agent comprising GM-CSF are separately used to collectively judge the results thus obtained, whereby the diagnosis can be made with higher precision.

EXAMPLES

The present invention will hereinafter be described in detail by the following Examples. However, the present invention is not limited to these examples.

Example 1

Establishment of NCL-4 producing cell line:

Peripheral blood mononuclear leukocytes (MNL, 100 cells/well) were cocultured with an irradiated (20,000 rad) human adult T cell leukemia cell line (MT2). This culture was performed in an RPMI-1640 solution containing 10% fetal calf serum (FCS) and 2 mM L-glutamine in a 96-well plate under conditions of 37° C. and moistened air containing 5% $CO_2$. A half of the medium was changed every 3 days. After 1–3 months, the growth of the cells became stable, and the expression of an ATL-antigen was observed in the greater part thereof. As the result of an HLA test (typing), it was confirmed that the cultured cells were derived from the peripheral blood leukocytes of the donor and not from the MT-2 cells. This cell line was cloned at a concentration of 0.5–1/well with irradiated (20,000 rad) autogenous MNL "filler" cells.

The cell line thus established was stored in an RPMI-1640 solution containing 10% FCS. In order to obtain medium conditions for the T cell line, the cells ($2 \times 10^5$ cells/ml) were cultured over 3 days at 37° C. in moistened air containing 5% $CO_2$ using a serum-free Iscove's-modified Dulbecco's medium (IMDM) containing 2 mM L-glutamine, a 25 mM Hepes buffer solution and $5 \times 10^{-5}$ M 2-mercaptoethanol.

Whether the established T cell line produces a neutrophil chemotactic factor or not was investigated by testing the culture solution thereof as to neutrophil chemotaxis (according to a method which will be described subsequently).

The culture solution of the MT-2 cells did not exhibit neutrophil chemotaxis. Some of the established T cell lines exhibited chemotaxis. In particular, CFR-24 of these T cell lines most notably exhibited neutrophil chemotaxis (FIG. 1). Therefore, CFR-24 was used in production of NCL-4 in the following examples. The phenotype of CFR-24 was analyzed. As a result, it was found that most of them had T cell markers such as CD2 (94.8%), CD3 (52.8%), CD4 (83.6%) and CD5 (87.9%), and some of them had CD8 (16.1%). On the other hand, CFR-24 had neither granulocyte/macrophage markers nor B cell markers such as CD16 (11.0%) and Leu7 (1.7%). Further, CFR-24 is considered to be in an activated state because it had CD25 (93.02%) and HLA-DR (100%). It was found from the above that CFR-24 belongs to a helper T cell lineage in activated form.

Example 2

Isoelectric Focusing of Neutrophil Chemotactic Lymphokines

Preparative isoelectric focusing was conducted using a carrier ampholyte (Bio-Lyte 3/10; Bio-Rad in Richmond) and a Rotofor system (Bio-Rad in Richmond). The CFR-24 cultured medium, which had been fully dialyzed against 1% glycine, was used in an amount of 50 ml. Twenty fractions were collected by the electrofocusing and fully dialyzed against a phosphate buffer solution (pH: 7.4), thereby investigating the neutrophil chemotaxis of the individual fractions.

As a result, it was recognized 4 fractions by which a neutrophil of a healthy person clearly exhibited chemotaxis (FIG. 1). Of the four fractions, fractions separately having a pI of 4–4.4, a pI of 4.6–5.0, a pI of 5.9–6.2 and a pI of 6.8–7.0 were designated NCL-1, NCL-2, NCL-3 and NCL-4, respectively.

Example 3

Properties of NCL-4
(1) Materials

Blood was collected by a vacuum blood collecting tube containing heparin. Separation of granulocytes was performed in the following manner. Added to 20 ml of a 3% dextran-PBS solution were 10 ml of the heparinized blood, and the mixture was fully blended and left at rest for 15 minutes, thereby obtaining a supernatant containing granulocytes. The supernatant was applied on 15 ml of a Ficoll pack (Pharmacia) and centrifuged at 550×g for 30 minutes, thereby dividing it into a lymphocyte layer and a granulocyte sediment. In order to remove erythrocytes mixed therein from the granulocyte sediment, 10 ml of cold water were first added, and the mixture was left over for 30 seconds to hemolyze the erythrocytes. Then, 10 ml of PBS concentrated twice were added to return to isotonicity. Further, 15 ml of a Hanks' solution were added, and the mixture was then centrifuged at 550×g for 5 minutes. The sediment was washed again with 15 ml of a Hanks' solution, thereby obtaining granulocytes. The granulocytes were suspended at a concentration of $2 \times 10^6$ cells/ml in an RPMI solution containing 10% FBS and used in a test of chemotactic capability and determination of CD16.

(2) Determination Methods

The molecular weight of NCL-4 was determined in the following manner. After a column of Cellulofine GCL-1000 (2.5×40 cm, Seikagaku Kogyo Co., Ltd.) was equilibrated with a 0.05 M Tris-HCl/0.1 M KCl solution (pH: 7.5), the NCL-4 was applied to fractionate every 3 ml, thereby identifying the molecular weight of NCL-4 by determining the chemotactic activity thereof.

Its affinity for heparin was identified by mixing NCL-4 (500 μl) and an Affinity Gel Heparin (Bio-Rad, 50 μl) at room temperature for 90 minutes, and then centrifuging the mixture to determine the chemotactic resultant supernatant and of a liquid dissolved out of the sediment by a treatment with 2M NaCl.

Test of Chemotactic Activity

A 24-well Transwell having a pore size of 3 μm manufactured by Coaster Co. was used. Added to outer wells thereof were 600 Al of a chemotactic factor [GM-CSF, TNF, 10 ng/ml (Genzyme); NCL-4, 100 μl/600 μl; IL-8, 3 ng/ml (Otuka Pharmaceutical Co., Ltd.); C5a, 3 ng/ml (Sigma); fMLP, 10 nM (Sigma); or LTB4, 100 pg/ml (Sigma)], and 100 μl of the granulocyte suspension were added to inner wells thereof, thereby reacting them for 2 hours in a $CO^2$ incubator at 37° C. After completion of the reaction, the inner wells were removed, and 0.5 ml of cold 0.1% BSA-0.1% $NaN_3$-PBS were added to the outer wells. After fully stirring, the number of cells in each of the outer wells was counted by a flow cytometer (Spectrum III). As a control, 0.05% BSA-PBS was used, and the above factors were diluted with this solution. The chemotactic capability was expressed in terms of a chemotaxis index which was obtained by dividing the number of cells migrated by the chemotactic factor by the number of cells migrated by the control.

Effect of inhibiting decrease in CD16 (effect of inhibiting apoptosis)

Placed in a 96-well culture dish (Corning) were 50 μl of the granulocyte suspension and 50 μl of a stimulating factor, thereby conducting culture for 24 hours at 370 in a $CO_2$ incubator. Thereafter, 0.5 ml of 1% BSA-0.1% $NaN_3$-PBS were added, and the mixture was fully stirred and then centrifuged (1,500 rpm, 5 minutes). After a supernatant was sucked out, and the sediment was fully stirred, 20 μl of an anti-CD16 antibody (Becton Dickinson) were added to conduct a reaction for 1 hour in ice water. After completion of the reaction, 1.0 ml of 1% BSA-0.1% $NaN_3$-PBS was added, and the mixture was fully stirred and then centrifuged (1,500 rpm, 5 minutes). After a supernatant was sucked out, and the sediment was fully stirred, 0.5 ml of 1% BSA-0.1% $NaN_3$-PBS were added to suspend the sediment, thereby analyzing the suspension by means of a flow cytometer (Spectrum III).

Production of IL-8

Placed in a 96-well culture dish (Corning) were 50 μl of the granulocyte suspension and 50 μl of a stimulating factor, thereby conducting culture for 24 hours at 370 in a $CO_2$ incubator. Thereafter, 0.1 ml of 1% BSA-0.1% $NaN_3$-PBS were added, the mixture was fully stirred and then centrifuged (1,500 rpm, 5 minutes), and 0.1 ml of a supernatant were taken out, thereby determining IL-8 by enzyme immunoassay.

Expression of CD11b

Heparinized blood was poured in 50-μl portions into tubes, and 20 μl of 0.05% BSA-PBS and a stimulating factor were added to each of the tubes, thereby conducting a reaction at 37° C. for 20 minutes. After completion of the reaction, the reaction mixture was washed with 1 ml of cold 0.1% BSA-0.1% $NaN_3$-PBS, and 20 μl of an anti-CD11b antibody (Becton Dickinson) were added to conduct a reaction for 1 hour in ice water. After completion of the reaction, the reaction mixture was hemolyzed with a hemolytic reagent and centrifuged. The sediment was then suspended in 0.5 ml of cold 0.1% BSA-0.1% $NaN_3$-PBS, thereby analyzing the suspension by means of a flow cytometer (Spectrum III).

Test for Measuring the Concentration of Calcium

Added to 200 μl of heparinized blood were 20 μl of 0.09 mM Fluo-3 AM (Dojindo), thereby loading the cells with Fluo-3 over 30 minutes at room temperature. Thereafter, the cells were hemolyzed, washed with a Hanks' solution and then suspended in 2 ml of 0.05% BSA-PBS. Added to 0.5 ml of the cell suspension were 5 μl of a stimulating factor, and analysis was immediately performed by means of a flow cytometer (Spectrum III).

Test for Measuring Membrane Potential

After 100 μl of heparinized blood were hemolyzed and washed with a Hanks' solution, it was suspended in 1 ml of 0.05% BSA-PBS and reacted with 1 μM Bis-oxanol (Mol. Prob) at room temperature for 30 minutes, thereby loading the cells with Bis-oxanol. Added to 0.5 ml of the cell suspension were 50 μl of a stimulating factor, and after 2 minutes, analysis was performed by means of a flow cytometer (Spectrum III).

Concentrations of Cytokines in the NCL-4 Fraction

One milliliter of the NCL-4 fraction was taken out to separately determine IL-lα, IL-1β, IL-6, IL-2, IL-8, TNF-α, GM-CSF, G-CSF, IFN-α and IFN-γ by enzyme immunoassay, and M-CSF by radioimmunoassay.

(3) Results

As shown in Table 1, NCL-4 has chemotactic activity, but does not increase an intracellular Ca concentration and a cell membrane potential unlike the already known chemotactic factors such as IL-8, C5a, fMLP and LTB4. NCL-4 has an effect of inhibiting decrease in CD16 (effect of inhibiting apoptosis) though such an effect is not recognized in the already known chemotactic factors such as IL-8, C5a, fMLP and LTB4. GM-CSF, G-CSF and TNF-α also have neutrophil chemotactic activity, but GM-CSF is different from NCL-4 in that GM-CSF does not induce the production of IL-8 from the neutrophil. As shown in Table 2, as the result of determining various cytokines contained in the NCL-4 fraction, it was found that neither TNF-α nor G-CSF is contained in the NCL-4 fraction, but GM-CSF and IL-2 are recognized. As shown in Table 1, however, IL-2 has no chemotactic activity. NCL-4 is also considered a substance having the nature different from the known substances from the viewpoints of the respective molecular weights, isoelectric points and affinity for heparin (Table 1).

TABLE 1

|  | NCL-4 | GM-CSF | G-CSF | TNF-α | IL-8 | IL-2 | C5a | fMLP | LTB4 |
|---|---|---|---|---|---|---|---|---|---|
| Granulocyte chemotactic activity (CI) | 9.9 | 11.3 | 6.5 | 7.1 | 49.2 | 0.0 | 36.4 | 34.0 | 28.4 |
| Expression of CD11B (Δ Mean channel) | 8.2 | 15.1 | 2.6 | 31.0 | 21.9 | — | 43.4 | 45.0 | — |
| Increase in intracellular Ca (% positive) | 0.0 | 0.0 | 0.0 | 0.0 | 59.0 | — | 80.0 | 84.0 | 40.0 |
| Increase in membrane potential (% positive) | 0.0 | 0.0 | 0.0 | — | 13.0 | — | 88.0 | 71.0 | — |
| Inhibition of apoptosis (% of inhibition) | 38.2 | 42.9 | — | 29.8 | 0.0 | 0.0 | 0.0 | 0.0 | — |
| Production of IL-8 (pg/ml) | 214 | <20 | — | 179 | — | — | — | — | — |
| Molecular weight (kb) | 50–80 | 22 | 19 | 36 | 6–8 | 15 | 8.6 | 0.4 | 0.3 |
| Isoelectric point | 6.8–7.0 | 3.4–4.5 | — | — | 8.6 | — | — | — | — |
| Affinity for heparin | None | None | — | — | Yes | — | — | — | — |

—: Not investigated.

TABLE 2

Various cytokines contained in the NCL-4 fraction

| | IL-1α (pg/ml) | IL-1β (pg/ml) | IL-6 (pg/ml) | IL-2 (pg/ml) | IL-8 (pg/ml) | TNF-α (pg/ml) | CM-CSF (pg/ml) | G-CSF (pg/ml) | M-CSF (pg/ml) | IFN-α (pg/ml) | IFN-γ (pg/ml) |
|---|---|---|---|---|---|---|---|---|---|---|---|
| NCL-4 | <10 | <20 | <20 | 759 | <20 | <20 | 34 | <20 | <0.2 | <20 | <20 |
| Sensitivity to measurement | 10 | 20 | 20 | 50 | 20 | 20 | 20 | 20 | 0.2 | 20 | 20 |

Example 4

Test of Neutrophil Chemotaxis

The human peripheral bloods used in this experiment were provided from patients and healthy persons unless expressly noted. Neutrophils were isolated from the bloods collected by vacuum blood collecting tubes containing heparin in accordance with the following process. Added to 20 ml of a 3% dextran-PBS solution were 10 ml of the heparinized blood, and the mixture was fully mixed and left at rest for 15 minutes, thereby obtaining a supernatant containing granulocytes. The supernatant was applied on 15 ml of a Ficoll pack (product of Pharmacia) and centrifuged at 550×g for 30 minutes, thereby dividing it into a lymphocyte layer and a neutrophil sediment. In order to remove erythrocytes from the neutrophil sediment, 10 ml of cold water were added, and the mixture was left over for 30 seconds to hemolyze the erythrocytes. Then, 10 ml of PBS concentrated twice were added to return to isotonicity. Further, 15 ml of a Hanks' solution were added, and the mixture was then centrifuged at 550×g for 5 minutes. The sediment was washed again with 15 ml of a Hanks' solution, thereby obtaining neutrophils. The neutrophils thus obtained were suspended at a concentration of $2 \times 10^6$ cells/ml in an RPMI solution containing 10% FBS and used in a test of chemotaxis. The purity of the neutrophils was at least 95%, and their survival rate was also at least 95%.

The chemotaxis was determined in accordance with the test of chemotactic activity in Example 3(2) or by the following process.

A 48-well microchemotaxis chamber equipped with a polyvinyl pyrrolidone-free Nuclepore filter having a pore size of 3 μm for neutrophils was used to conduct analysis. After the neutrophils ($1-2 \times 10^6$ cells/ml) were incubated at 37° C. for 2 hours, cells adhered to the lower surface through the filter were stained with a Diff-Quick (The Green Cross Corporation) and counted through an optical microscope of 5 high power field (hpf, 40×10). The measurement result as to the neutrophil chemotaxis was expressed as the mean number±SD of migrated cells/hpf in triplicate. In this result of the chemotaxis test, the neutrophil chemotaxis index of the patients was expressed as CI. The CI was calculated out in accordance with the equation: (chemotactic activity to NCL-4 or GM-CSF)/(chemotactic activity to PBS).

Example 5

Comparison of Patients Suffering From Drug-Induced Granulocytopenia With Healthy Persons as to Neutrophil Chemotaxis The neutrophil chemotaxis to the four neutrophil chemotactic factors derived from CFR-24 of various patients and healthy persons was investigated. The result is shown in Table 3.

Incidentally, the patients are patients suffering from congestive heart failure, to which Arkin Z had been administered. Arkin Z is an agent useful for treating heart failure and is known to cause agranulocytosis (about 0.3%).

TABLE 3

| | Group of patients attacked by granulocytopenia | | Group of patients not attacked by granulocytopenia | |
|---|---|---|---|---|
| NCL-4 | | | | |
| 95% CI (upper limit < 4.20) | 16/21 | 76.2% | 12/48 | 25.0% |
| 99% CI (upper limit < 4.59) | 17/21 | 81.0% | 15/48 | 31.3% |
| GM-CSF | | | | |
| 95% CI (upper limit < 8.31) | 8/10 | 80.0% | 19/33 | 57.6% |
| 99% CI (upper limit < 9.36) | 8/10 | 80.0% | 20/33 | 60.6% |

Figure 2:
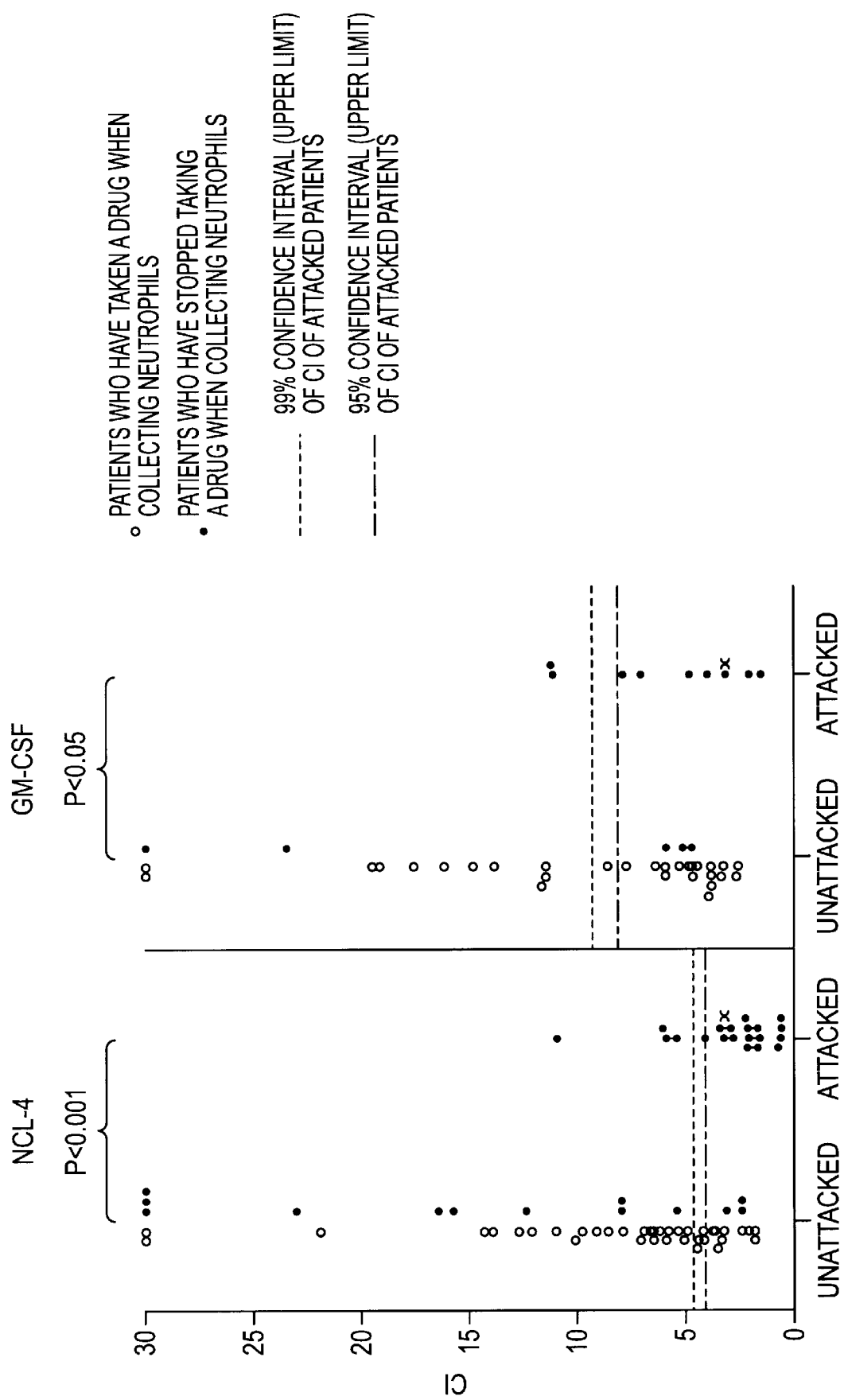

As a result, with respect to the neutrophils of the groups of healthy persons and patients not attacked by granulocytopenia (patients suffering from heart failure and not attacked by granulocytopenia upon the administration of Arkin Z), chemotaxis was induced by the four different NCLs derived from CFR-24. With respect to the neutrophils of the group of patients attacked by granulocytopenia (patients suffering from heart failure and attacked by granulocytopenia after the administration of Arkin Z), however, chemotaxis was induced by NCL-1 and NCL-2, but not induced by NCL-3 and NCL-4. Therefore, the neutrophil chemotaxis to NCL-4 and the neutrophil chemotaxis to C5a were comparatively analyzed between the group of the attacked patients and the group of the unattacked patients using the index CI. As a result, with respect to C5a, there was no difference in the CI of the neutrophils among the three groups. On the other hand, with respect to NCL-4 and GM-CSF, a marked difference was recognized between the group of the attacked patients and the group of the unattacked patients as shown in Table 3 and FIG. 2. More specifically, the CI to NCL-4 in the group of the attacked patients was smaller than 4.59 (the upper limit of 99% conficence interval (CI) of the group of the attacked patients) in 17 cases of 21 cases, while the CI to NCL-4 in the group of the unattacked patients was smaller than 4.59 in 15 cases of 48 cases. Besides, the CI to GM-CSF in the group of the attacked patients was smaller than 9.36 (the upper limit of 99% confidence interval (CI) of the group of the attacked patients) in 8 cases of 10 cases, while the CI to GM-CSF in the group of the unattacked patients was smaller than 9.36 in 20 cases of 33 cases.

From the above results, it can be diagnosed that any patient suffering from heart failure and having a CI value to NCL-4 of 5 or smaller has a possibility of being attacked by granulocytopenia when Arkin Z is used in treatment for heart failure. It can also be diagnosed that any patient suffering from heart failure and having a CI value to GM-CSF of 10 or smaller has a possibility of being attacked by granulocytopenia when Arkin Z is used in the treatment.

Example 6

Test of the Ability to Express CD11b

Heparinized blood collected by a vacuum blood collecting tube containing heparin was poured in 50-μl portions into tubes, and 20 μl of 0.05% BSA-PBS, NCL-4 or GM-CSF (10 ng/ml, Genzyme) were added to the tube, thereby conducting a reaction at 37° C. for 20 minutes. After completion of the reaction, the reaction mixture was washed with 1 ml of cold 0.1% BSA-0.1% NaN$_3$-PBS, and 20 μl of an anti-CD11b antibody (Becton Dickinson) were added to conduct a reaction for 1 hour in ice water. After completion of the reaction, the reaction mixture was hemolyzed with a hemolytic reagent and centrifuged. The sediment was then suspended in 0.5 ml of cold 0.1% BSA-0.1% NaN$_3$-PBS, thereby analyzing the suspension by means of a flow cytometer (Spectrum III). The results in the 0.05% BAS-PBS group was used as a control, and the expression of CD11b was expressed in terms of % of the amount of CD11b more expressed than the amount of CD11b expressed in the control.

The expression of CD11b was comparatively analyzed between the group of patients attacked by granulocytopenia (patients suffering from heart failure and attacked by granulocytopenia after the administration of Arkin Z) and the group of patients not attacked by granulocytopenia (patients suffering from heart failure and not attacked by granulocytopenia upon the administration of Arkin Z). The result is shown in Table 4.

TABLE 4

|  | Group of attacked patients | | Group of unattacked patients | |
| --- | --- | --- | --- | --- |
| NCL-4 | | | | |
| 95% CI (upper limit < 18.59) | 7/10 | 70.0% | 9/33 | 27.3% |
| 99% CI (upper limit < 20.85) | 9/10 | 90.0% | 10/33 | 30.3% |
| GM-CSF | | | | |
| 95% CI (upper limit < 11.34) | 8/10 | 80.0% | 12/33 | 36.4% |
| 99% CI (upper limit < 12.73) | 9/10 | 90.0% | 13/33 | 39.4% |

Figure 3:
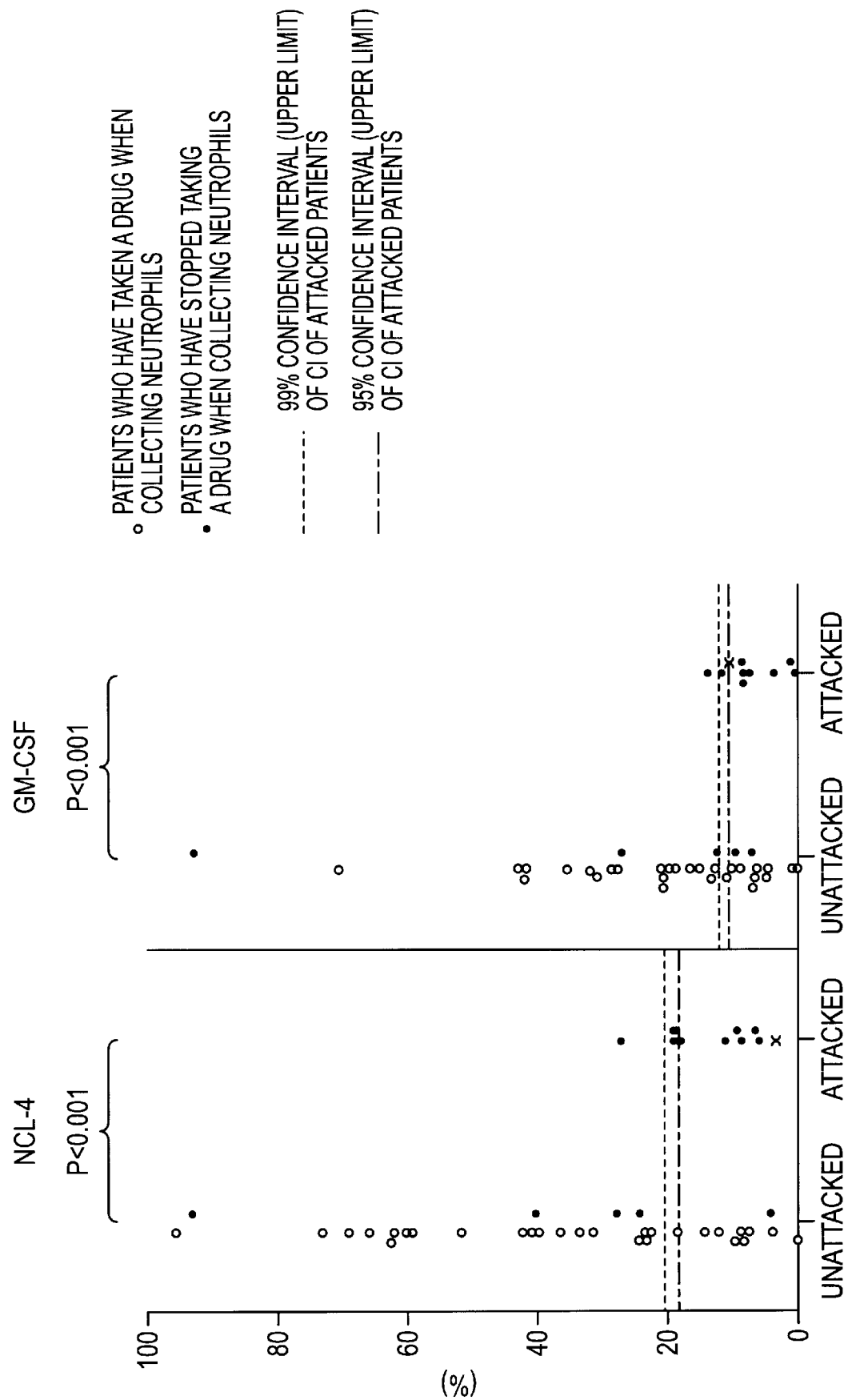

As a result, with respect to NCL-4 and GM-CSF, a marked difference was recognized between the group of the attacked patients and the group of the unattacked patients as shown in Table 4 and FIG. 3. More specifically, the expression of CD11b by NCL-4 in the group of the attacked patients was less than 20.85 (the upper limit of 99% confidence interval of the group of the attacked patients) in 9 cases of 10 cases, while the expression of CD11b by NCL-4 in the group of the unattacked patients was less than 20.85 in 10 cases of 33 cases. Besides, the expression of CD11b by GM-CSF in the group of the attacked patients was less than 12.73 (the upper limit of 99% conficence interval of the group of the attacked patients) in 8 cases of 10 cases, while the expression of CD11b by GM-CSF in the group of the unattacked patients was less than 12.73 in 13 cases of 33 cases.

From the above results, it can be diagnosed that any patient suffering from heart failure and having low reactivity (chemotactic activity, expression of CD11b) to NCL-4 or GM-CSF has a possibility of being attacked by granulocytopenia when Arkin Z is used in treatment for heart failure.

INDUSTRIAL APPLICABILITY

When the diagnostic agent according to the present invention is used for a patient, whether the patient has a possibility that drug-induced granulocytopenia may be caused or not can be diagnosed prior to the administration of a drug. Therefore, the patient can be safely treated without causing any side effect.

What is claimed is:

1. An isolated neutrophil chemotactic lymphokine having an isoelectric point at 6.8–7.0, wherein said lymphokine has the properties of:

a) increasing neither intracellular calcium ion concentration nor cell membrane potential;

b) inhibiting apoptosis by decreasing CD16 expression;

c) inducing expression of CD11b d) having no affinity for heparin; and e) having a molecular weight of 50 kd to 80 kd as measured by gel filtration.

2. A method of diagnosing whether a subject is susceptible to drug-induced granulocytopenia, which comprises measuring reactivity of a neutrophil from said subject to GM-CSF or the lymphokine of claim 1.

3. The method of diagnosing according to claim 2, wherein the reactivity of the neutrophil is determined by chemotaxis of or the expression rate of CD11b of the neutrophil as an index of reactivity.

* * * * *

UNITED STATES PATENT AND TRADEMARK OFFICE
CERTIFICATE OF CORRECTION

PATENT NO. : 6,060,258
DATED : May 09, 2000
INVENTOR(S) : Mitsuomi HIRASHIMA

It is certified that error appears in the above-identified patent and that said Letters Patent is hereby corrected as shown below:

In the title, delete

"NEUTROPHIL CHEMOTACTIC LYMPHOKINE, AND METHOD FOR THE DIAGNOSIS OF DRUG HYPERSENSITIVE GRANULOCYTOPENIA USING THE SAME (as amended)", and insert therefor --NEUTROPHIL CHEMOTACTIC LYMPHOKINE, AND METHOD FOR DIAGNOSING DRUG-INDUCED GRANULOCYTOPENIA COMPRISING THE SAME (as amended)--.

Signed and Sealed this

Twenty-fourth Day of April, 2001

Attest:

NICHOLAS P. GODICI

Attesting Officer     Acting Director of the United States Patent and Trademark Office